United States Patent [19]

Ufkin

[11] Patent Number: 5,320,628
[45] Date of Patent: Jun. 14, 1994

[54] MULTIPLE MOVEMENT SINGLE CONTROL POSITIONING DEVICE

[76] Inventor: Kevin Ufkin, 6312 S. College, Tempe, Ariz. 85283

[21] Appl. No.: 82,887

[22] Filed: Jun. 28, 1993

[51] Int. Cl.⁵ .................. A61B 17/00; A61B 19/00
[52] U.S. Cl. ............................. 606/130; 604/116; 606/1
[58] Field of Search .............. 606/1, 130, 96–98, 606/104; 604/116; 128/DIG. 26

[56] References Cited

U.S. PATENT DOCUMENTS

| | | |
|---|---|---|
| 2,697,433 | 12/1954 | Zehnder .............................. 606/130 |
| 3,017,887 | 1/1962 | Meyer .................................. 606/130 |
| 3,073,310 | 1/1963 | Mocarski . | 
| 3,196,875 | 7/1965 | Pfeiffer ............................... 606/130 |
| 4,526,169 | 7/1985 | Narishige et al. ................... 606/130 |
| 4,723,544 | 2/1988 | Moore . | 
| 4,809,694 | 3/1989 | Ferrara ............................... 606/130 |
| 4,955,891 | 9/1990 | Carol . | 
| 5,030,223 | 7/1991 | Anderson et al. .................. 606/130 |

Primary Examiner—Stephen C. Pellegrino
Assistant Examiner—Glenn Dawson
Attorney, Agent, or Firm—LaValle D. Ptak

[57] ABSTRACT

A multiple-movement, single clamp, implement-positioning device is constructed to permit sliding movement of the base portion of a main body member on a guide rail. An upper portion of the main body member is rotatably mounted on the base portion and includes a hollow chamber with a compressible sphere pivotally mounted in it. The compressible sphere has a bore through it; and an elongated cylindrical shaft is slidably and rotatably mounted in the bore in the compressible sphere. A single control member, in the form of a threaded rod, extends through the top of the upper portion of the main body member to engage the sphere to compress it into engagement with an extension on the base portion. This compresses the bore around the shaft, locks the pivotal rotation of the sphere, locks the upper portion of the main body member to the base portion and the base portion to the rail on which it is positioned. All of this effected through a simple rotation or manipulation of a single control handle to simultaneously release and secure all of the five sliding, tilting and rotational movements which may be effected by the device.

20 Claims, 2 Drawing Sheets

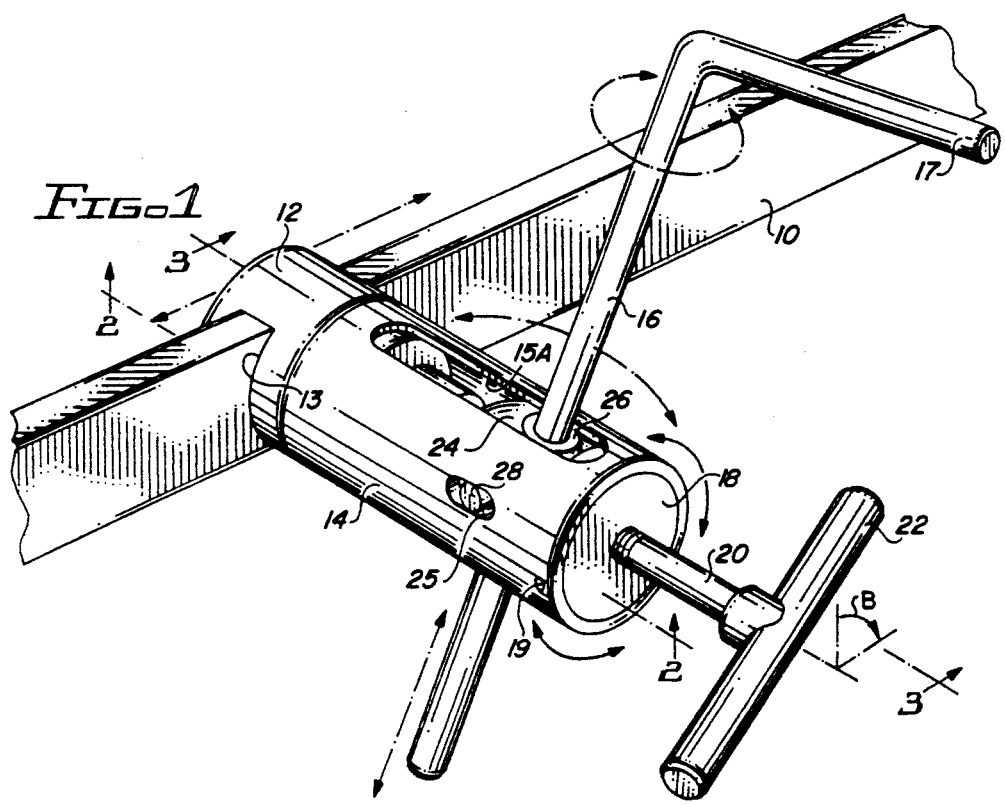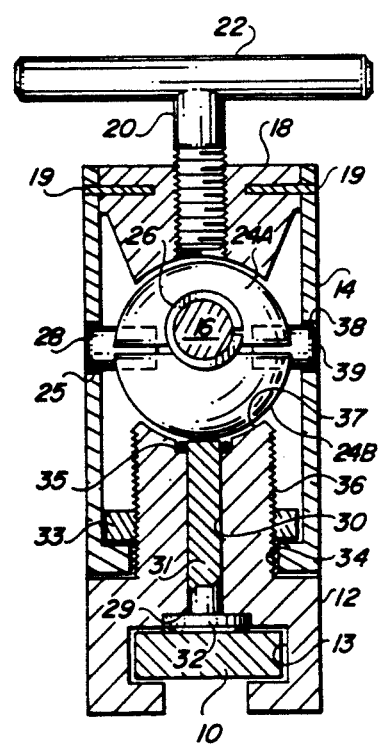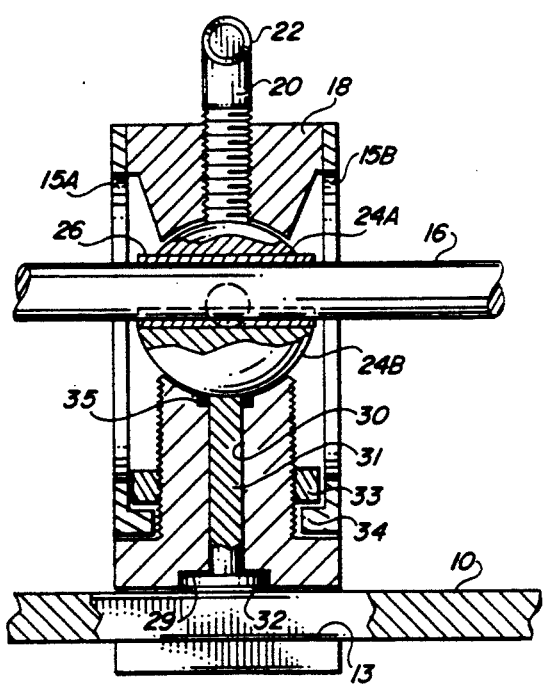

MULTIPLE MOVEMENT SINGLE CONTROL POSITIONING DEVICE

BACKGROUND

Applications exist, particularly in the field of neurosurgery, for mechanisms capable of effecting accurate positioning of an implement, such as the working end of a surgical instrument, an electrode, a needle, or the like. Because the implement must be spatially moved to any desired position over the skull of the patient, the mechanism for effecting this positioning must be capable of multiple movements in a three dimensional coordinate system. Consequently, sliding movements with respect to a fixed rail over the operating table, coupled with rotational movements, tilting movements and the like, all must be precisely controlled in order to place the implement at the desired position and angle at which it is to be used.

Mechanisms for positioning such implements typically require a number of separate adjustments, with separate locking of each of the different movements necessary to effect and hold the three-dimensional positioning. As a result, such mechanisms are difficult and cumbersome to use and require substantial skill and considerable manipulation on the part of the physician or other user.

Three surgical instrument positioning devices, capable of multiple movement in a three dimensional coordinate system, are disclosed in the U.S. patents to Mocarski No. 3,073,310; Moore No. 4,723,544; and Carol No. 4,955,891. The devices disclosed in each of these patents are relatively complex arrangements of rotational and sliding members, requiring multiple clamps to secure and release the different movements of various levers comprising the components of the positioning devices in order to effect the desired positioning. All of these devices are cumbersome to use, because of the multiple clamps or cams which must be operated in order to lock the different motions of the different parts in place. Since all of these parts and motions are separately locked or released, the manipulation of the components and the accurate positioning of the instrument, with which they are designed for use, requires a substantial amount of skill and experience.

An effort to reduce the complexity of operation of a spatial positioning implement for positioning an electrode in a precise manner is disclosed in the U.S. patent to Pfeiffer No. 3,196,875. This patent is directed to a manipulating device, which is slidably mounted on a carriage on a semi-circular track. The carriage may be moved to different positions along the track and rotated or tipped about the track. Once the location of the carriage has been selected, it is locked in place on the track by a threaded locking handle.

In the Pfeiffer device, the instrument itself is carried on the tip of an extension of an elongated rod, which is slidably and rotatably mounted in a bore through a split compressible sphere. The sphere is held in a clamp having a split through it, which may be drawn together or released by means of a clamping lever. When the clamping lever is released, a handle on the end of the positioning rod may be used to move the rod back and forth through the bore in the sphere, and to rotate it until the instrument is located in the desired position. Once this has been effected, clamp jaws are contracted by manipulation of a lock lever to squeeze the compressible sphere. This holds the sphere in place, so that it cannot be rotated. The sphere also compresses against the bore through it to prevent further rotation and sliding of the rod extending through it.

Thus, two different mechanisms are required in Pfeiffer to complete the positioning of the device; and two different clamping members must be operated in order to effect that positioning. Manipulation of the two together effects the proper position of the instrument. Then two separate operations by the person utilizing the positioning device are necessary to lock it into place, and, subsequently, to release it.

Accordingly, it is desirable to provide a positioning device capable of positioning an implement in a three-dimensional coordinate system quickly and accurately, and in which the position of the implement then may be secured by means of the operation of a single locking member or control member.

SUMMARY OF THE INVENTION

It is an object of this invention to provide an improved position control mechanism.

It is another object of this invention to provide an improved implement positioning mechanism.

It is an additional object of this invention to provide an improved implement positioning mechanism for positioning an implement in a three-dimensional coordinate system.

It is a further object of this invention to provide an improved implement positioning system capable of positioning an implement in a three-dimensional coordinate system and in which operation of a single control member releaseably locks all of the movements of said device in a single operation.

In accordance with a preferred embodiment of this invention, a device for positioning an implement consists of a main body member. This main body member, in turn, includes a base portion and an upper portion, which is rotatably mounted on the base portion. The upper portion has a hollow chamber in it; and an elongated slot extends through the upper portion to communicate with this chamber. A compressible sphere is located in the hollow chamber for rotational movement about the center of the sphere, which also has a bore through it. An elongated cylindrical shaft then is slidably and rotatably mounted in the bore through the sphere, and passes through the slot in the upper portion of the main body member. A single control member is used to releaseably lock the base portion and upper portion of the main body member together, simultaneously, with the locking of the sphere and the cylindrical shaft in preselected positions.

BRIEF DESCRIPTION OF THE DRAWINGS

FIG. 1 is a perspective view of a preferred embodiment of the invention;

FIG. 2 is a cross-sectional view taken along the line 2—2 of FIG. 1;

FIG. 3 is a cross-sectional view taken along the line 3—3 of FIG. 1; and

DETAILED DESCRIPTION

Figure 4:
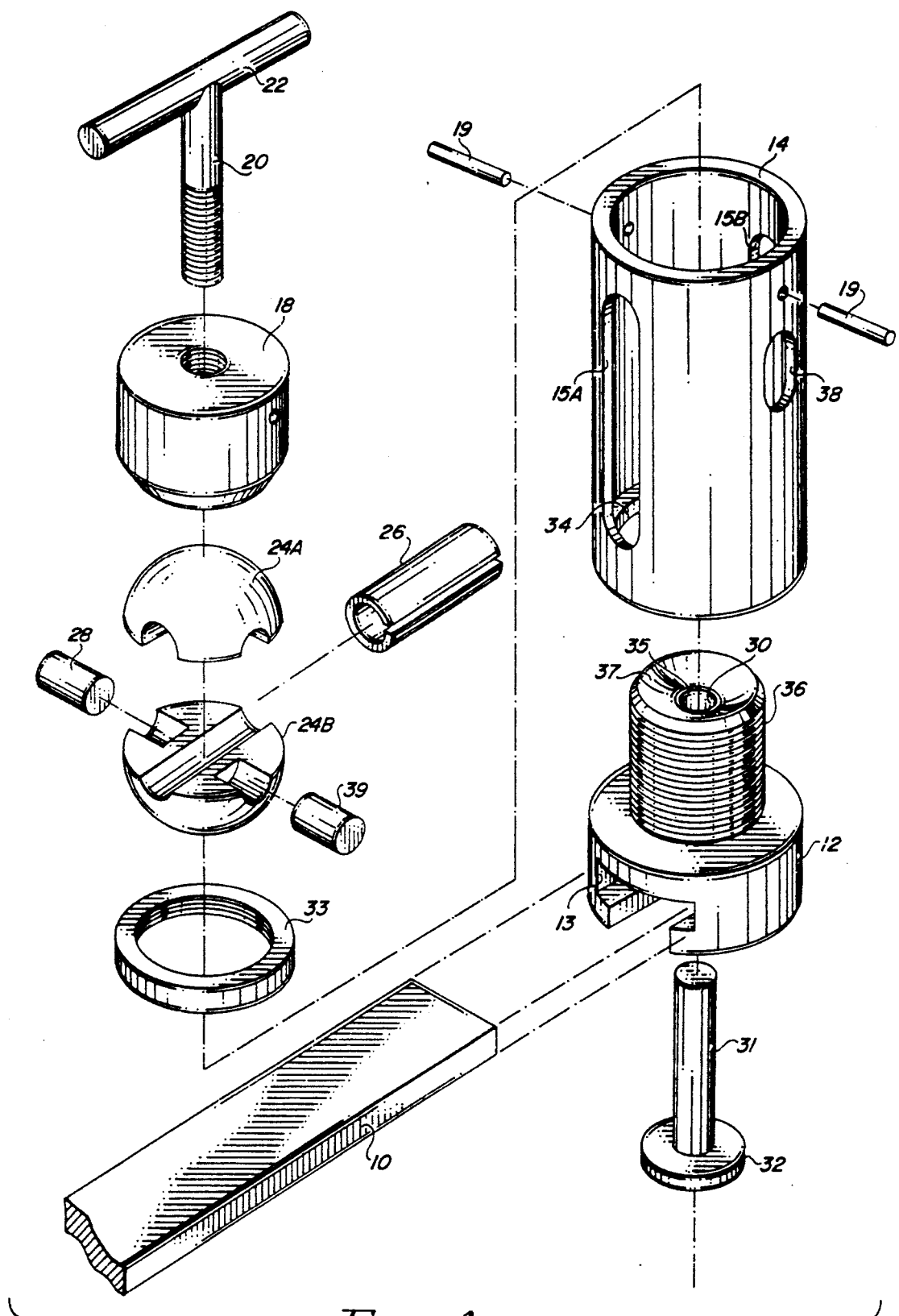
FIG. 4 is an exploded view of the embodiment shown in FIG. 1.

Reference now should be made to the drawings, in which the same reference numbers are used throughout the different figures to designate the same components. The embodiment illustrated in the four figures of the drawings is a device which is particularly suitable for use in a variety of neurosurgical applications for positioning an implement quickly and precisely at a predetermined selected area of the skull or the brain of a patient. The device is capable of five different simultaneous movements for effecting a precise three-dimensional positioning of an instrument quickly and effectively. Once the positioning has been accomplished, all five of the different motions, which the device is capable of performing, are secured or locked in place by means of the manipulation of a single control lever. Consequently, the positioning quickly and easily is accomplished; and once that has been effected, the locking of all of the different motions in place easily may be effected, since no multiple lever or multiple cam locking devices are used.

To accomplish the foregoing, the device consists of a unique arrangement and interrelationship of parts. Typically, a positioning device for surgical instruments, particularly used for neurosurgery, is mounted on a support rail 10. The support rail 10 is placed in a fixed location relative to an operating table (not shown) and forms the base reference for the location of the surgical instrument or other implement carried by the device.

The positioning device itself comprises a main body having a lower or base portion 12 and an upper portion 14, rotatably mounted on the base portion 12. The base portion 12 is slidably placed on the rail 10, which passes through a slot 13 through the base portion perpendicular its central axis. The slot 13 has inwardly turned legs on it to engage the opposite side of the rail 10 from the side on which the remainder of the device of FIG. 1 is located. These inwardly turned legs are shown most clearly in FIGS. 2 and 4. When the device is released, the base portion 12 may be moved back and forth along the rail 10 in the direction of the arrow to any desired position.

As illustrated in FIGS. 2, 3 and 4, the base portion 12 has a central cylindrical extension 36 on it, which is of less diameter than the outer diameter of the portion 12. This extension 36 is externally threaded, and terminates in a spherically concave upper surface 37. In the assembly of the device, the upper portion 14 is placed over the extension 36 to abut the shoulder on the base portion 12. The upper portion 12 is hollow, and has an inwardly turned flange 34 around its lower end, with the diameter of the opening of the flange selected to pass freely over the extension 36 on the base portion 12.

When the upper portion 14 is in place, as shown in FIGS. 2 and 3, a threaded retaining ring or locking shoulder 33 is turned in place to the position shown in FIGS. 2 and 3 to rotatably secure the upper portion 14 onto the base portion 13. The threaded portion 33 is moved into close proximity to the inwardly turned flange 34; but sufficient clearance is provided to permit free axial rotation of the portion 14 with respect to the base 13 when the ring or shoulder 33 is in place.

After placement of the ring 33, a compressible sphere, made of an upper part 24A and a lower part 24B, is placed into the hollow chamber in the upper portion 14, in the location shown most clearly in FIGS. 2 and 2. As is readily apparent from an examination of FIG. 4, this compressible sphere is split horizontally in a plane located above a plane passing through the center of the sphere; so that the section 24A is smaller than the section 24B. Together, however, the two sections comprise a complete sphere. Also, as is clearly shown in FIGS. 2, 3 and 4, there is a central bore through the sphere, in which an elongated split cylindrical bushing 26 is placed.

The bushing 26 has an elongated solid cylindrical shaft 16 passing through it for slidable movement and for rotational movement, as indicated most clearly in FIG. 1. The shaft 16 typically is bent at right angles to terminate in a projection 17. The projection 17 then may have any suitable implement or surgical instrument attached to it for positioning by the device. It is to be noted that the shaft 16, passing through the bushing 26 in the bore through the sphere 24A/24B, also passes through elongated slots 15A and 15B, located on diametrically opposite sides of the cylindrical upper portion 14, and aligned with the axis of the cylindrical upper portion 14.

To facilitate accurate assembly and disassembly of the device if the shaft 16 ever is completely removed after assembly, the sphere 24A/24B also has a pair of partial bores located on an axis through the center of the sphere 24A/24B for receiving a pair of locating pins 28 and 39. These pins respectively extend into short elongated slots 25 and 38 on opposite sides of the upper portion 14 of the device. These locating pins 28 and 39 permit rotation of the sphere 24A/24B freely about a line passing through the center of the sphere and the slots 15A and 15B.

Some longitudinal movement of the sphere 24A/24B parallel to the axis of portion 14 also is permitted by the elongated slots 26 and 38. The slots 25 and 38 are shown in exaggerated proportion to the diameter of the circular pins 28 and 39 for the purposes of illustration of the operation of the device. Typically, these slots are only slightly elongated to permit a small amount of movement of the sphere 24A/24B along the longitudinal axis of the upper portion 14.

Next in the assembly of the device, a plug or top 18 is placed in the open upper end of the upper portion 14. This plug 18 then may be held in place by means of pins 19, as illustrated in FIGS. 2 and 4; or it may be keyed by means of other suitable keys, or secured by means of brazing, welding or the like. It is to be noted from an examination of FIGS. 2 and 3 that the lower end of the plug 18, used to close the top of the cylinder for the upper portion 14, has a spherically concave surface on it, which is complementary to the outer surface of the upper portion 24A of the sphere 24A/24B. Similarly, the surface 37 on the extension 36 is a complementary mating surface for the outer surface of the spherical section 24B of the compressible sphere.

The device described thus far is capable of five different independent or simultaneous movements, indicated by the various double-ended arrows in FIG. 1. As mentioned previously, the base portion 12 may be moved anywhere desired along the rail 10. Similarly, a 360° rotation of the part 14, with respect to the base portion 13, may be effected. In addition, the rod 16 may be moved to the limits of its length back and forth in a sliding motion through the bushing 26 in the sphere 24A/24B, and also may be rotated 360° to pivot the end 17, as desired. The final motion is a rocking motion on the sphere 24A/24B. The extent of this motion is limited by the relative dimensions of the sphere 24A/24B, the rod or shaft 16 and the length of the slots 15A and 15B.

Once the position of the implement-carrying end 17 on the shaft or rod 16 is effected, all of the above motion is locked in place by turning a single handle 22 to rotate a threaded shaft 20, which is threaded through a center opening in the plug 18 in the top of the upper portion 14 of the main body of the device. As shown in FIG. 2, the shaft 20 is in its released position to permit all of the above five different positioning movements to take place. When the shaft is turned clockwise to tighten it, the lower end of the shaft 20 engages the top 24A of the compressible sphere, pushing it downwardly against the split cylindrical bushing 26, causing the bushing 26 to squeeze together as it presses onto the bottom portion 24B of the compressible sphere, which in turn is pressed into engagement with the surface 37 of the extension 36. The bottom portion 24B of the sphere also presses downwardly on a rod 31 terminating in a circular flange 32, which presses onto the upper surface (as viewed in FIGS. 2, 3 and 4) of the rail 10 to clamp it tightly into the slot 13 against the inwardly turned edges of the housing 12 located on the opposite side of the rail 10, as most clearly shown in FIGS. 2 and 4. The rod 31 passes through an opening 30 in the extension 36, and it is held in place; so that it does not drop out of the apparatus, by means of a rubber O-ring bushing 35, which may be located anywhere along the length of the bore 30 through the extension 36. As illustrated in FIGS. 2 and 3, the O-ring 35 is located near the upper end of the bore 30; but this location is not critical.

It is to be noted that when the handle 22, attached to the shaft 20, is rotated approximately one-quarter turn, all of the different relative motions of the different parts of the device are clamped in place. When the lower end of the rod 20 presses on the top portion 24A of the split collapsible sphere 24A/24B, the bottom portion presses against the surface 37, as described previously. This causes the upper portion 14 of the housing to move relatively upwardly to the position shown in FIG. 3; so that the inwardly turned flange 34 tightly engages the lower side of the locking shoulder formed by the ring 33 to clamp the upper portion 14 against rotation relative to the base portion 12 of the housing.

When the two sections of the sphere 24A/24B are pressed together, the split bushing 26 is tightly squeezed onto the rod or shaft 16. The shaft 16 cannot be rotated, and cannot be slidably moved in the bushing 26. When the top portion 24A and the bottom portion 24B of the sphere are clamped tightly by means of the end of the shaft 20 and the surface 37 on the extension 36, the sphere 24A/24B cannot be rotated; so that the rod or shaft 16 cannot be rocked in the slots 15A/15B. Finally, the downward force of the lower sphere portion 24B on the upper end of the rod 31 causes the flange 32 to tightly press onto the upper surface of the rail 10 to clamp the entire device against sliding movement on the rail 10. All of this is effected by a single control member, namely the shaft 20 operated by the handle 22.

Release of all of the different movements, to which the device is capable, is effected simply by turning the handle 22 counterclockwise approximately one quarter turn. This releases all of the compressive forces which have been described above; so that the various motions which have been described, once again, may be effected.

Preferably, all of the various parts, which have been shown and described above, are made of metal, such as steel or aluminum. The bushing 26 is a spring-like bushing, which expands to its original shape upon release of the locking pressure, when the shaft 20 is rotated counterclockwise to the position shown in FIG. 2, to unlock all of the different motions. Consequently, the bushing 26 effectively functions as the return mechanism for releasing the different parts to permit the different motions which have been described above. The device is illustrated in FIG. 1 in approximately full size. A typical positioning device, suitable for use with instrument positioning for a variety of different neurosurgery techniques is approximately four inches long, with a diameter of the cylindrical portion 14 of approximately one inch. Thus, it is readily apparent that the device is a very compact mechanism. It should be noted that while the discussion of the preferred embodiment has been made in conjunction with the spatial positioning of an instrument on the end 17 of the rod 16, particularly suited for neurosurgery, any application which requires accurate positioning of an implement in a spatial or three-dimensional location may be effected by means of this device.

The foregoing description of the preferred embodiment of the invention is to be considered as illustrative, and not as limiting. Various changes and modifications will occur to those skilled in the art without departing from the true scope of the invention. For example, the use of a threaded shaft 20, operated by a lever 22 for effecting the release and locking of the mechanism, may be replaced by a cam operation for some applications, if desired. So long as the downward pressure, which is effected by the end of the shaft 20 relative to the housing sections 12 and 14, is accomplished, other mechanisms may be used. Also, it should be noted that the locating pins 28 and 39, which hold the sphere 24A/24B in position even when a shaft 16 is completely removed from the sphere, may be eliminated if desired. If they are eliminated, it is possible for the sphere to rotate in the chamber of the housing 14; so that the bushing 26 is not aligned with the slots 15A and 15B. It then would be necessary to reach through the slots 15A or 15B to rotate the sphere until proper alignment of the bushing 26 was attained, to permit re-insertion of a shaft 16. The pins 28 and 39, however, are not essential for the clamping and release operation which has been described.

Different techniques for assembling the various parts together may be used, so long as the relative motions and the manner of clamping or locking those motions simultaneously with a single operating lever or control member may be used. Other changes and modifications will occur to those skilled in the art, without departing from the true scope of the invention as defined in the appended claims.

I claim:

1. A device for positioning an implement including in combination;

a main body member comprising a base portion and an upper portion rotatably mounted about an axis of rotation on said base portion, said upper portion having a hollow chamber therein with a first elongated slot through said upper portion on at least one side of said chamber in a plane parallel to the axis of rotation of said upper portion;

a compressible sphere having a bore therethrough and located in the chamber in said upper portion for rotational movement therein;

an elongated cylindrical shaft slidably and rotatably mounted in said bore through said sphere and passing through said first elongated slot in said upper portion; and a single control member on one of said base portion and said upper portion and operable between a release condition and locking condition, the release condition of said control member permitting relative rotation of said base portion and said upper portion, rotation of said sphere, and sliding and rotation of said shaft in said bore through said sphere, and the locking condition of said control member compressing said sphere and securing said base portion, said upper portion, said sphere and said shaft in preselected relative positions.

2. The combination according to claim 1 wherein the locking condition of said control member compresses said sphere between said upper and lower portions of said main body member to compress said bore on said cylindrical shaft and draw said upper and lower portions of said main body member together, thereby preventing rotation of said upper portion relative to said base portion.

3. The combination according to claim 2 wherein said upper portion of said main body member is cylindrical with an upper end and a lower end, the lower end thereof terminating in an inwardly turned flange, and said base portion has a first shoulder thereon from which a projection rises to extend into the hollow chamber of said upper portion past said inwardly turned flange; and further including a locking shoulder on said projection of said base portion located over said inwardly turned flange on the lower end of said upper portion, with said projection having a sphere-engaging mating surface for a portion of said compressible sphere and the upper end of said main body member having a mating surface for said compressible sphere with said compressible sphere located between said mating surfaces on said base portion and said upper portion; and wherein said single control member in the locking condition thereof pulls said upper portion upwardly relative to said base portion to cause said inwardly turned flange thereon to engage said locking shoulder and presses said compressible sphere into tight engagement with the mating surface on the projection in said base portion.

4. The combination according to claim 3 wherein said base portion has an upper and a lower end and said projection is on the upper end of said base portion; and further including a bore through said base portion between the sphere-engaging surface thereof and the lower end thereof and a push rod inserted in said bore through said base portion for movement therein, said push rod engaged by said sphere when operation of said control member to the locking condition thereof causes said sphere to be pressed into engagement with the mating surface on the upper end of said projection on said base portion for exerting a downward force at the lower end of said base portion.

5. The combination according to claim 4 wherein said compressible sphere comprises first and second sections with a portion of said bore located in each section, and further including a cylindrical longitudinally split bore insert located in the bore in said first and second sections of said sphere with said elongated cylindrical shaft passing through said cylindrical bore insert.

6. The combination according to claim 5 wherein said upper portion of said main body member has a closed top with a threaded bore therethrough and said single control member comprises a rotatable threaded shaft extending through said threaded bore for engagement with said compressible sphere, such that when said threaded shaft is rotated into engagement with said compressible sphere the secure condition of said control member exists, and when said threaded shaft is rotated out of engagement with said compressible sphere the release condition of said control member exists.

7. The combination according to claim 6 wherein said projection on said base portion is an externally threaded cylindrical member and said locking shoulder comprises an internally threaded locking ring positioned above said inwardly turned flange of said upper portion of said main body member.

8. The combination according to claim 7 further including a handle on said threaded shaft for facilitating operation of said control member.

9. The combination according to claim 8 further including a slot through the lower end of said base portion perpendicular to the bore therethrough and communicating with said push rod such that when a mounting rail is placed in said slot, said base member may be adjusted in position along said mounting rail with said control member in said release condition of operation, and with said push rod exerting a force on said mounting rail in said slot to secure said base portion in a preselected position on said mounting rail with said control member operated to the locking condition thereof.

10. The combination according to claim 9 further including a second elongated slot through said upper portion on a side of the chamber in said upper portion opposite said first elongated slot and aligned therewith to permit passage of said shaft therethrough.

11. The combination according to claim 10 wherein said base portion and said upper portion of said main body member are cylindrical.

12. The combination according to claim 11 wherein said base portion and said upper portion of said main body member, said sphere and said shaft all are made of metal.

13. The combination according to claim 1 further including a second elongated slot through said upper portion on a side of the chamber in said upper portion opposite said first elongated slot and aligned therewith to permit passage of said shaft therethrough.

14. The combination according to claim 1 wherein said upper portion of said main body member is cylindrical with an upper end and a lower end, the lower end thereof terminating in an inwardly turned flange, and said base portion has a first shoulder thereon from which a projection rises to extend into the hollow chamber of said upper portion past said inwardly turned flange; and further including a locking shoulder on said projection of said base portion located over said inwardly turned flange on the lower end of said upper portion, with said projection having a sphere-engaging mating surface for a portion of said compressible sphere and the upper end of said main body member having a mating surface for said compressible sphere with said compressible sphere located between said mating surfaces on said base portion and said upper portion; and wherein said single control member in the locking condition thereof pulls said upper portion upwardly relative to said base portion to cause said inwardly turned flange thereon to engage said locking shoulder and presses said compressible sphere into tight engagement with the mating surface on the projection in said base portion.

15. The combination according to claim 14 wherein said base portion has an upper and and a lower end and said projection is on the upper end of said base portion; and further including a bore through said base portion between the sphere-engaging surface thereof and the lower end thereof and a push rod inserted in said bore through said base portion for movement therein, said push rod engaged by said sphere when operation of said control member to the locking condition thereof causes said sphere to be pressed into engagement with the mating surface on the upper end of said projection on said base portion for exerting a downward force at the lower end of said base portion.

16. The combination according to claim 15 further including a slot through the lower end of said base portion perpendicular to the bore therethrough and communicating with said push rod such that when a mounting rail is placed in said slot, said base member may be adjusted in position along said mounting rail with said control member in said release condition of operation, and with said push rod exerting a force on said mounting rail in said slot to secure said base portion in a preselected position on said mounting rail with said control member operated to the locking condition thereof.

17. The combination according to claim 14 wherein said upper portion of said main body member has a closed top with a threaded bore therethrough and said single control member comprises a rotatable threaded shaft extending through said threaded bore for engagement with said compressible sphere, such that when said threaded shaft is rotated into engagement with said compressible sphere the locking condition of said control member exists, and when said threaded shaft is rotated out of engagement with said compressible sphere the release condition of said control member exists.

18. The combination according to claim 17 further including a handle on said threaded shaft for facilitating operation of said control member.

19. The combination according to claim 18 wherein said projection on said base portion is an externally threaded cylindrical member and said locking shoulder comprises an internally threaded locking ring positioned above said inwardly turned flange of said upper portion of said main body member.

20. The combination according to claim 1 wherein said compressible sphere comprises first and second sections with a portion of said bore located in each section, and further including a cylindrical longitudinally split bore insert located in the bore in said first and second sections of said sphere with said elongated cylindrical shaft passing through said cylindrical bore insert.

* * * * *